United States Patent
Doering et al.

(10) Patent No.: US 11,147,756 B2
(45) Date of Patent: Oct. 19, 2021

(54) COSMETIC COMPOSITIONS WITH REDUCED OILY OR GREASY FEEL ON THE SKIN

(71) Applicant: Henkel AG & Co. KGaA, Duesseldorf (DE)

(72) Inventors: Thomas Doering, Dormagen (DE); Sandra Mausberg, Haan (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 212 days.

(21) Appl. No.: 16/197,131

(22) Filed: Nov. 20, 2018

(65) Prior Publication Data

US 2019/0151216 A1 May 23, 2019

(30) Foreign Application Priority Data

Nov. 23, 2017 (DE) ...................... 10 2017 220 988.7

(51) Int. Cl.
| | |
|---|---|
| *A61K 8/37* | (2006.01) |
| *A61K 8/86* | (2006.01) |
| *A61K 8/891* | (2006.01) |
| *A61Q 15/00* | (2006.01) |
| *A61K 8/06* | (2006.01) |
| *A61Q 19/00* | (2006.01) |

(52) U.S. Cl.
CPC ................ *A61K 8/37* (2013.01); *A61K 8/062* (2013.01); *A61K 8/891* (2013.01); *A61Q 19/00* (2013.01); *A61K 2800/5922* (2013.01); *A61Q 19/007* (2013.01)

(58) Field of Classification Search
CPC . A61K 8/37; A61K 8/375; A61K 8/86; A61K 8/891; A61K 2800/5922; A61K 2800/30; A61K 2800/34; A61K 8/046; A61Q 15/00
See application file for complete search history.

(56) References Cited

U.S. PATENT DOCUMENTS

| | | |
|---|---|---|
| 2007/0292358 A1 | 12/2007 | Emmerling et al. |
| 2013/0028855 A1* | 1/2013 | Yarlagadda ............ A61K 8/342 424/66 |
| 2013/0330290 A1 | 12/2013 | Alden-Danforth et al. |
| 2017/0007515 A1 | 1/2017 | Menon et al. |
| 2018/0042835 A1 | 2/2018 | Doering et al. |

FOREIGN PATENT DOCUMENTS

| | | |
|---|---|---|
| DE | 102004061228 A1 | 6/2006 |
| DE | 102013217316 A1 | 3/2015 |
| DE | 102015205477 A1 | 9/2016 |
| WO | 2018076083 A | 5/2018 |

* cited by examiner

*Primary Examiner* — Bethany P Barham
*Assistant Examiner* — Peter Anthopolos
(74) *Attorney, Agent, or Firm* — Lorenz & Kopf, LLP

(57) ABSTRACT

The present disclosure relates to a cosmetic composition containing an oil mixture in a total amount of from about 40 to about 99% by weight, in relation to the total amount of the cosmetic composition, without taking into consideration any propellant possibly provided, wherein the oil mixture of at least two selected esters, at least one linear polydimethylsiloxane with a viscosity of from about 1 to less than about 20 cSt, also PPG-14 butyl ether, wherein cyclic polydimethylsiloxanes are contained in a total amount, in relation to the total amount of the cosmetic composition, of from 0 to about 0.4% by weight, and wherein PPG-14 butyl ether and linear polydimethylsiloxanes are contained in selected ratios by weight to one another.

17 Claims, No Drawings

COSMETIC COMPOSITIONS WITH REDUCED OILY OR GREASY FEEL ON THE SKIN

CROSS-REFERENCE TO RELATED APPLICATION

This application claims priority to German Patent Application No. 10 2017 220 988.7, filed Nov. 23, 2017, which is incorporated herein by reference in its entirety.

TECHNICAL FIELD

The present disclosure relates to cosmetic compositions for personal care which contain a special oil mixture and are particularly suited for use in antiperspirants.

BACKGROUND

Washing, cleaning and caring for the human body is an important basic need, and cosmetics manufacturers are always trying to meet the constantly changing and evolving requirements of consumers by supplying innovative and/or improved products.

Cosmetic care products often contain a higher proportion of one or more oils, which are intended to provide a pleasant and caring feel on the skin. These oils or oil mixtures are usually used as a basis of the formulations and also as carriers for active substances in the care products, for example for antiperspirant (aluminium) salts. A disadvantage of most conventional oils is their oily or greasy nature, which indeed provides richness and conditioning properties, but often leaves behind an oily or greasy film, which is unpleasant to the touch and transfers to objects or textiles coming into contact with it and soils them. This, in particular in combination with active substances such as the above-mentioned aluminium salts, can lead to stubborn stains which are difficult to wash out from textiles.

As an alternative to the conventional oils, in order to reduce the formation of oil or grease films on the skin, oils are used that are volatile at room temperature (25° C.) and a pressure of 1013 mbar, such as cyclic silicone oils. A disadvantage of the use of exclusively volatile oils in cosmetic compositions lies in the fact that volatile oils often do not have a satisfactory skin-caring effect and that they, in particular in high concentrations, can lead in aerosol applications to a dusty spray jet that is less well focused. In addition, attempts have been made to substitute the use of cyclic polydimethylsiloxanes, such as hexamethylcyclotrisiloxane, octamethylcyclotetrasiloxane, decamethylcyclopentasiloxane and dodecamethylcyclohexasiloxane in cosmetics, since these substances have a delayed biodegradability.

There is thus also a need for cosmetic compositions for body care which are exemplified by a pleasant feel on the skin with reduced oily or greasy nature which and at the same time ensure an increased biodegradability.

BRIEF SUMMARY

A cosmetic composition is provided herein. The cosmetic composition includes an oil mixture in a total amount of from about 40 to about 99% by weight, in relation to the total amount of the cosmetic composition, without taking into consideration any propellant possibly provided. The oil mixture includes a) at least two esters, which are formed from at least one linear or branched, saturated or unsaturated monocarboxylic acids with 3 to 30 carbon atoms and at least one linear or branched, saturated or unsaturated alcohol with from 1 to 30 carbon atoms. The oil mixture further includes b) at least one linear polydimethylsiloxane, wherein the linear polydimethylsiloxane or a mixture of two or more linear polydimethylsiloxanes, at 25° C. and a pressure of 1013 mbar, has a kinematic viscosity of from about 1 to less than about 20 cSt. The oil mixture further includes c) PPG-14 butyl ether. The oil mixture further includes d) optionally, cyclic polydimethylsiloxane in a total amount, in relation to the total amount of the cosmetic composition, of no greater than 0.4% by weight, wherein the total amount of the esters, in relation to the total amount of the oil mixture, is from about 45 to about 70% by weight, and the ratio by weight of PPG-14 butyl ether to the total amount of all linear polydimethylsiloxanes lies in the range of from about 1.2 to about 2.4.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide a cosmetic composition with improved biodegradability which has a high content of skin-nourishing oils, which ensure good adhesion on the skin or good absorption into the skin and thus prevent the formation of oil films or grease films.

A further objective was to formulate antiperspirants, in particular oil-based antiperspirants, that have good compatibility with the skin, such that they are exemplified by a lasting pleasant feel on the skin which is not too dry and which is not too oily or greasy.

It has now surprisingly been found that the above-mentioned objects are achieved to an excellent degree with the aid of a cosmetic composition that contains an oil mixture of specific composition.

The oil mixture can be incorporated well into a large number of cosmetic care compositions and can even be used as the primary base for cosmetic compositions. It demonstrates an excellent skincare effect alongside a reduced oily or reduced greasy feel on the skin. Here, the cosmetic composition is exemplified by good biodegradability. In addition, the oil mixture when used as an antiperspirant composition, for example in particular in anhydrous antiperspirants or in anhydrous antiperspirant aerosols, demonstrates an excellent antiperspirant effect alongside pleasant application and good, lasting wearing comfort.

A first subject matter of the present disclosure is therefore a cosmetic composition which includes an oil mixture of specific composition in a total amount of from about 40 to about 99% by weight in relation to the total amount of the cosmetic composition. This amount does not take into consideration any propellant provided, which in other words means that no possible propellant to be added or already added is included in the total amount of the cosmetic composition.

As mentioned above, the oil mixture has a specific composition, which is defined conclusively and includes
a) at least two esters, which are formed from at least one linear or branched, saturated or unsaturated monocarboxylic acids with 3 to 30 carbon atoms, which optionally can contain one or more hydroxyl groups, and at least one linear or branched, saturated or unsaturated alcohol with 1 to 30 carbon atoms, and furthermore b) at least one linear polydimethylsiloxane, wherein the linear polydimethylsiloxane or a mixture of two or more linear polydimethylsiloxanes, at 25° C. and a pressure of 1013 mbar, has a kinematic viscosity of from about 1 to less than about 20 cSt, c) PPG-14 butyl ether and d) optionally, cyclic polydimethylsiloxane in a total amount, in relation to the total amount of the cosmetic composition, of no greater than about 0.4% by weight, preferably 0% by weight.

Suitable cosmetic compositions are understood as contemplated herein to be preferably skin treatment compositions that have a high content of hydrophobic active substances (oils), for example skin creams, makeups, lipsticks, further decorative cosmetic products, such as eyeshadows, peels, skin lotions, deodorants, antiperspirants, hair oils, styling products and/or pomades. In particular for the above-mentioned cosmetic compositions, a total amount of the oil mixture, in relation to the total amount of the cosmetic composition, of from about 40 to about 99% by weight has proven to be advantageous, because hereby the caring nature of the cosmetic composition for skin and hair is particularly effective. With the exception of the components contained in the oil mixture, the cosmetic composition does not contain any further oils, fats or waxes, which also includes silicone oils.

Furthermore, the total amount of cyclic polydimethylsiloxane, that is to say the total amount of all cyclic polydimethylsiloxanes contained in the oil mixture, in relation to the total amount of the cosmetic composition, is 0 to about 0.4% by weight, and is preferably 0% by weight. This means that there is no addition of any cyclic polydimethylsiloxanes in the cosmetic composition as contemplated herein. Merely unavoidable technical impurities of polydimethylsiloxanes, which fluctuate within the above-mentioned scope of at most about 0.4% by weight and for example are introduced by the constituents of the oil mixture essential to the present disclosure, may be contained. Explicitly, cyclic polydimethylsiloxanes however are not added, on account of their low biodegradability.

PPG-14 butyl ether is a propylene glycol ether of butyl alcohol which can be exemplified by the following formula: $C_4H_9(OC(CH_3)CH_2)_nOH$, wherein n is 14. On account of the propylene glycol content, PPG-14 butyl ether is exemplified by a moderately hydrophilic nature, which is very well suited for dispersion of ingredients of the cosmetic compositions that are hydrophilic to a greater or lesser extent, such as nourishing additives, inclusive of active substances, or also colorants, such as pigments or dyes. In particular, salts, including in particular aluminium salts, as are used in antiperspirants, can also be dispersed in the oil mixture by means PPG-14. butyl ether. In addition, PPG-14 butyl ether makes an important contribution to the nongreasy feel on the skin of the oil mixture as contemplated herein.

At least one linear polydimethylsiloxane is contained as further essential constituent of the oil mixture as contemplated herein. This means that an individual linear polydimethylsiloxane alone or also a mixture of two or more polydimethylsiloxane can be contained, wherein the one linear polydimethylsiloxane or the mixture of two or more linear polydimethylsiloxanes has, at a temperature of about 25° C. and a pressure of about 1013 mbar, a kinematic viscosity of from about 1 to less than about 20 cSt. Linear polydimethylsiloxanes of this kind are classed as low-viscosity silicone oils.

The addition of low-viscosity linear polydimethylsiloxanes to the oil mixture provides the oil mixture and therefore also the composition as contemplated herein with particularly advantageous properties in respect of the application thereof. These include in particular the rheological properties of the oil mixture or the cosmetic composition as contemplated herein and the spreading behaviour. The composition as contemplated herein on the one hand can hereby be applied very easily to skin and hair and uniformly distributed, without having to apply a high shear force, and on the other hand does not have such a low viscosity that it drips off or rolls away from the application site.

Here, the term "spreading" means the ability of a liquid substance to spread out after contact with a surface. The spread value is used as a measure for the spreading behaviour of a liquid substance on a surface. The spread value can be determined in accordance with a method known in the prior art (for example as described in DE102013217316) and is usually specified in $mm^2/10$ min.

In addition, the addition to the oil mixture of linear polydimethylsiloxanes which, at about 25° C. and at a pressure of about 1013 mbar, have a kinematic viscosity of less than about 20 cSt increases the ease with which white stains on textiles, caused for example by the deposition of aluminium salts from antiperspirants, can be washed out.

However, since linear polydimethylsiloxanes do not penetrate the skin or hair on account of their chemical nature, but merely adhere to the surface thereof, a total amount of all linear polydimethylsiloxanes contained in the oil mixture is advantageously not too high. Here, it has proven to be advantageous if the ratio by weight of PPG-14 butyl ether to the total amount of all linear polydimethylsiloxanes lies in the range of from about 1.2 to about 2.4, preferably from about 1.3 to about 2.2, and particularly preferably from about 1.5 to about 2.0.

In order to additionally prevent a separation of the at least one linear polydimethylsiloxane, the oil mixture contains, as further essential constituent, at least two esters, which are formed from at least one linear or branched, saturated or unsaturated monocarboxylic acids with from about 3 to about 30 carbon atoms, which optionally can contain one or more hydroxyl groups, and at least one linear or branched, saturated or unsaturated alcohol with from about 1 to about 30 carbon atoms. Esters are exemplified, depending on their hydrocarbon groups, by predominantly lipophilic properties, wherein their lipophilicity can be selectively controlled by selection of the light of the hydrocarbon chains of the used carboxylic acid and of the used alcohol. On account of the carboxylate group, a certain hydrophilic nature is additionally introduced into the esters. The esters used as contemplated herein in the oil mixture contribute effectively to the dispersibility of the one or more linear polydimethylsiloxanes, such that hardly any, or even no separation occurs, even after a longer standing time.

The esters used as contemplated herein are additionally exemplified by a very good feel on the skin. They are also distributed easily and homogeneously over the skin and also on hair, without having a drying effect and also without leaving behind a heavy oily or greasy film, since they are even absorbed in part into the skin. Precisely an oily or greasy nature of the oil mixture is significantly reduced by the combination of the esters used as contemplated herein and of the at least one linear polydimethylsiloxane used as contemplated herein, compared to oil mixtures that contain conventional waxes, fats and oils. In addition, by employing the esters that are to be used, a dry feel of the cosmetic composition when this is applied can be prevented, as is the case with the use of volatile silicone oils, such as cyclic polydimethylsiloxanes.

In order to attain these effects, it is therefore also essential that the total amount of the esters, in relation to the total amount of the oil mixture, is from about 45 to about 70% by weight and preferably from about 50 to about 65% by weight. The advantageous properties of the esters are hereby very effective and are also reflected in the cosmetic composition. The specified total amount of the esters is additionally advantageous for the ease of washing out the cosmetic composition from textiles, since the above-mentioned esters can disperse very well in surfactant-containing solution.

The esters used as contemplated herein particularly preferably include liquid oils. A liquid oil is understood as contemplated herein to be a liquid substance which under normal conditions is miscible with bidistilled water to an extent less than 1% by weight.

All details regarding the aggregate states of substances (solid, liquid, gaseous) in this application relate to normal conditions. "Normal conditions" in the sense of the present application are a temperature of 25° C. and a pressure of 1013 mbar.

The cosmetic composition as contemplated herein is exemplified, in account of the contained oil mixture of specific composition, by very good application properties, such as the capability for good and uniform distribution and good adhesion to skin and hair, and, if provided, extremely low oily or greasy feel on the skin. The use of at least one linear polydimethylsiloxane also contributes to this. Due to the omission of cyclic polydimethylsiloxanes and the high content of esters in the oil mixture, the cosmetic composition is additionally also effectively biodegradable. Furthermore, on account of its lipophilic and hydrophilic constituents, the oil mixture of specific composition enables the stable formulation of hydrophilic active substances and further ingredients into the cosmetic composition, such that the cosmetic composition as contemplated herein is suitable for different applications.

In accordance with a preferred embodiment, the oil mixture contains at least one ester a-1) and at least one ester a-2). The ester a-1) is selected here from esters formed from at least one linear or branched, saturated or unsaturated monocarboxylic acid with 8 to 20 carbon atoms, which optionally can contain one or more hydroxyl groups, and at least one linear or branched saturated or unsaturated alcohol with from 6 to 20 carbon atoms. The ester a-2) is selected from esters formed from at least one linear or branched, saturated or unsaturated monocarboxylic acid with from 10 to about 20 carbon atoms, which optionally can contain one or more hydroxyl groups, and at least one linear or branched, saturated or unsaturated alcohol with from 1 to 5 carbon atoms. The ester a-1) is thus more lipophilic than the ester a-2), and therefore the lipophilicity or the hydrophilicity of the oil mixture can be adjusted very easily by a suitable combination of the esters a-1) and a-2), and therefore the cosmetic compositions having a high lipophilic content and also cosmetic compositions having a high lipophilic content can be more easily formulated. This is advantageous depending on the intended application of the cosmetic composition and an active substance addition possibly intended for this purpose.

Particularly suitable esters a-1) are selected from 2-ethylhexyl laurate, 2-ethylhexyl myristate, 2-ethylhexyl palmitate, 2-ethylhexyl cocoate, 2-ethylhexyl stearate, 2-ethylhexyl isostearate, hexyldecyl laurate, hexyldecyl stearate, isooctyl stearate, isononyl isononanoate, isononyl stearate, isotridecyl nonanoate, 2-octyldodecyl palmitate, isocetyl stearate and/or mixtures of these esters. Esters a-2) are preferably selected from isopropyl myristate, isopropyl palmitate and isopropyl stearate and/or mixtures thereof. The above-mentioned esters can be incorporated well into the oil mixture, distribute well over skin and hair, and are particularly well suited for stabilising in the oil mixture the linear polydimethylsiloxanes used as contemplated herein. In addition, the combination of these esters in particular in antiperspirants demonstrates particularly good coverage of white powder residues on the skin and on textiles.

Among the aforementioned esters a-1), 2-ethylhexylpalmitate is particularly preferred. 2-ethylhexylpalmitate is exemplified by a particularly nourishing nature, without having a greasy or oily effect. 2-ethylhexylpalmitate can be well distributed over skin and hair, is absorbed well into the skin, and also does not weigh down hair considerably. Among the above-mentioned esters a-2), isopropylmyristate is particularly preferred. Isopropylmyristate is exemplified by a balanced property profile in respect of high spreading and thus good capability for distribution over the skin and hair, and in addition is very nourishing, without weighing down the hair or skin. In addition, isopropylmyristate can be formulated particularly homogeneously with the at least one linear polydimethylsiloxane used as contemplated herein.

In accordance with a further advantageous embodiment, the linear polydimethylsiloxane or the mixture of two or more linear polydimethylsiloxanes, at 25° C. and a pressure of 1013 mbar, has a kinematic viscosity of from about 1 cSt to less than about 15 cSt, preferably of about 2 cSt to less than about 10 cSt, and in particular of about 5 cSt. The lower is the kinematic viscosity of the linear polydimethylsiloxane, the thinner it is, and the more it spreads when applied to the skin or hair. High spreading can be of particular advantage for a surface application. The lower is the kinematic viscosity, the higher however is the vapour pressure of the linear polydimethylsiloxane, which is of importance for stable incorporation into the oil mixture and additionally also into the cosmetic composition. The kinematic viscosity of the at least one linear polydimethylsiloxane is particularly preferably at least about 2 cSt and in particular about 5 cSt. The kinematic viscosity is determined here at 25° C. by employing a capillary viscometer.

Particularly suitable linear polydimethylsiloxanes with a kinematic viscosity of about 5 cSt are commercially obtainable, for example under the trade name Xiameter® PMX 200 Sil Fluid 5 CS from the company Dow Corning, under the trade name AEC Dimethicone (5 CS) from the company A & E Connock (Perfumery & Cosmetics) Ltd.), under the trade name Dimethisil DM-5 from the company Innospec Performance Chemicals, under the trade name SF1000N-5 cSt from the company KCC Corporation and under the trade name Si-Tec DM 5 from the company Ashland Inc.

A further advantageous embodiment is exemplified in that the total amount of the linear polydimethylsiloxanes with a kinematic viscosity of from about 1 cSt to less than about 20 cSt, in relation to the total amount of the oil mixture, is from about 5 to about 25% by weight, preferably from about 7 to about 20% by weight, and more preferably from about 10 to about 17% by weight. Due to the total amount of the linear polydimethylsiloxanes with a kinematic viscosity of from about 1 cSt to less than about 20 cSt of at least about 5% by weight and in particular of at least about 7% by weight, and even more preferably of at least about 10% by weight, the rheological properties of the oil mixture, which also have an effect on the rheological properties of the cosmetic composition, can be set particularly advantageously. The oil mixture is exemplified hereby by a particularly good spreadability over the skin and hair, without the oil mixture being deemed to be dry in nature, this often resulting in an unpleasant application feel. The oil mixture slides on skin and hair over the application area when applied, without leaving behind a heavy oily or greasy film. A lasting formation of oily or greasy films can be prevented advantageously in that the total amount of the linear polydimethylsiloxanes with a kinematic viscosity of from about 1 cSt to less than about 20 cSt is not selected to be too high, and is preferably at most about 25% by weight, more preferably at most about 20% by weight, and even more preferably at most about 17% by weight. The total amount of the linear polydimethylsiloxanes with a kinematic viscosity of from about 1 cSt to less than about 20 cSt, in relation to the total amount of the oil mixture, thus particularly advantageously lies in a range of from about 10 to about 17% by weight.

In order to improve the dispersability of, in particular, hydrophilic ingredients in the cosmetic composition, including in particular salts, such as aluminium salts, as are used in antiperspirant, the total amount of PPG-14 butyl ether, in relation to the total amount of the oil mixture, in accordance with a further advantageous embodiment, can lie advantageously in a range of from about 15 to about 30% by weight. The higher here is the content of PPG-14 butyl ether, the better is the dispersability of hydrophilic ingredients, but the higher also is the risk of separation of the at least one linear polydimethylsiloxane. The total amount of the PPG-14 butyl ether is thus preferentially at most about 30% by weight, preferably at most about 28% by weight, and more preferably at most about 25% by weight. With a total amount of the PPG-14 butyl ether in a range of from about 20 to about 25% by weight, the desired amounts of linear polydimethylsiloxanes with a kinematic viscosity of from about 1 cSt to less than about 20 cSt can be incorporated very well and homogeneously in the oil mixture.

A particularly pleasant feel on skin can be attained in particular in that the ratio by weight of ester a-1) to ester a-2) is set to a range of from about 1 to about 7, preferably from about 1 to about 5, and more preferably from about 1 to about 3.

In accordance with a further advantageous embodiment, the cosmetic composition is exemplified in that the oil mixture comprises
  the at least two esters in a total amount of from about 40 to about 80% by weight, preferably from about 50 to about 70% by weight,
  PPG-14 butyl ether in an amount of from about 15 to about 30% by weight, preferably from about 18 to about 28% by weight, more preferably from about 20 to about 25% by weight, and
  one or more linear polydimethylsiloxanes with a kinematic viscosity of from about 1 cSt to less than about 20 cSt.

Here, the linear polydimethylsiloxane or a mixture of two or more linear polydimethylsiloxanes, at a temperature of about 25° C. and a pressure of about 1013 mbar, has a kinematic viscosity of from about 1 to less than about 20 cSt, and the total amount of the linear polydimethylsiloxanes is from about 5 to about 25% by weight, preferably from about 7 to about 20% by weight, and more preferably from about 10 to about 17% by weight.

An oil mixture composed of the above-mentioned components in the stated total amounts, which relate to the total amount of the oil mixture, are exemplified by a high storage stability alongside a particularly good application spectrum. The oil mixture and thus also the cosmetic composition containing the oil mixture is easily and homogeneously spreadable without high pressure or high shear forces, is also well absorbed into the skin, and offers the possibility for incorporation of hydrophilic ingredients, such as various active substances, in particular including salts such as aluminium salts, such that the cosmetic composition can be formulated with a broad application spectrum and very good feel on skin, which is neither too dry nor too oily or greasy. In addition, stains on textiles coming into contact with the cosmetic composition can be avoided by the above-sated cosmetic composition.

The above-mentioned advantageous properties of the oil mixture are particularly effective when the oil mixture is present in an amount of from about 50 to about 85% by weight, preferably from about 60 to about 75% by weight, more preferably from about 65 to about 70% by weight, in relation to the total amount of the cosmetic composition.

This is advantageous in particular for the preferred embodiment in which the cosmetic composition is anhydrous. "Anhydrous" in the sense of the present disclosure means, here, that the total amount of water, in relation to the total amount of the cosmetic composition, is from 0 to about 5% by weight, and in particular 0% by weight. Here, the content of water of crystallisation, hydration water or similarly molecularly bound water that can be contained in the constituents used, in particular in any included antiperspirant active substances, cannot be taken into consideration.

Anhydrous formulations not only have the advantage that they are less susceptible to bacterial contamination, from a microbiological perspective, and therefore do not have to be mixed with preservatives, or at least only have to be mixed with preservatives to a reduced extent, but are also advantageous in respect of a pleasant feel on skin, which is richer as compared to water-containing compositions, without weighing down the skin.

In a particularly preferred embodiment, the cosmetic composition additionally contains at least one antiperspirant active substance, such that the cosmetic composition is suitable in particular as an antiperspirant. Among the antiperspirant active substances, antiperspirant aluminium salts such as in particular aluminium chlorohydrate and aluminium sesquichlorohydrate, are particularly preferred on account of their high efficiency and their phenomenal spectrum of efficacy. In order to attain a particularly good antiperspirant effect, the at least one antiperspirant active substance is contained preferably in a total amount, in relation to the total amount of the cosmetic composition, of from about 10 to about 40% by weight. This means that, if a number of antiperspirant active substances are contained in combination, their total amount, in relation to the weight of the cosmetic composition, likewise lies in a range of from about 10 to about 40% by weight.

Antiperspirant active substances that are preferred as contemplated herein are the water-soluble astringent inorganic and organic salts of aluminium, zirconium and zinc, or any mixtures of these salts. Particularly preferred antiperspirant active substances are selected from aluminium chlorohydrates, for example aluminium sesquichlorohydrate, aluminium chlorohydrex propylene glycol (PG) or aluminium chlorohydrex polyethylene glycol (PEG), aluminium sesquichlorohydrex PG or PEG, aluminium PG dichlorohydrex or aluminium PEG dichlorohydrex, aluminium hydroxide, and are also selected from aluminium zirconium chlorohydrates, such as aluminium zirconium trichlorohydrate, aluminium zirconium tetrachlorohydrate, aluminium zirconium pentachlorohydrate, aluminium zirconium octachlorohydrate, aluminium zirconium chlorohydrate glycine complexes such as aluminium zirconium trichlorohydrex glycine, aluminium zirconium tetrachlorohydrex glycine, aluminium zirconium pentachlorohydrex glycine, aluminium zirconium octachlorohydrex glycine, potassium aluminium sulfate ($KAl(SO_4)_2 \cdot 12H_2O$, alum), sodium aluminium chlorohydroxy lactate, aluminium bromide hydrate, aluminium chloride, aluminium sulfate, aluminium lactate, sodium aluminium chlorohydroxy lactate, zinc chloride, zinc sulfocarbolate, zinc sulfate and zirconium chlorohydrate.

As contemplated herein, "water solubility" is understood to mean a solubility of at least 5% by weight in water at 20° C., i.e. that quantities of at least 5 g of the antiperspirant active substance are soluble in 95 g of water at 20° C. The antiperspirant active substances are preferably used as powdered raw materials.

It has surprisingly been found that, in particular in anhydrous cosmetic compositions, high total amounts of antiperspirant active substances, such as aluminium salts, can be incorporated into the cosmetic composition in a particularly homogeneous and stable manner. Without being bound to the theory, it is assumed that the PPG-14 butyl ether provides a good dispersability of the antiperspirant active substances in the oil mixture, which is improved by the combination of the esters. Compositions of antiperspirant active substances, such as aluminium salts, merely with PPG-14 butyl ether and linear polydimethylsiloxanes, by contrast have led to insufficient stability, in particular in respect of storage of the cosmetic composition. In addition, a good feel on skin upon application, which is not too dry, can be attained merely by the combination of the at least one linear polydimethylsiloxane with the esters with use of the PPG-14 butyl ether, wherein there is also no formation of a heavy oily or greasy film. The oil mixture of specific composition is therefore advantageous in particular for the formulation of antiperspirant compositions.

In light of the above-disclosed embodiment, the cosmetic composition as contemplated herein is therefore particularly advantageously provided in the form of an antiperspirant composition, for example preferably in the form of an anhydrous antiperspirant stick or in the form of an anhydrous antiperspirant aerosol. The oil mixture of specific composition has proven to be particularly advantageous for these applications.

Anhydrous antiperspirant aerosols can be advantageous for some application forms. Antiperspirant aerosols that are suitable as contemplated herein are preferably packaged in aerosol cans. The cans can be made of tinplate or of aluminium. Furthermore, the cans in accordance with a particularly preferred embodiment can be coated internally in order to minimise the risk of corrosion.

The aerosol cans are preferably equipped with a suitable spray head. Depending on the spray head, discharge rates of from about 0.1 g/s to about 2.0 g/s, based on fully filled cans, are preferred.

In a further preferred embodiment, the cosmetic composition as contemplated herein can also contain at least one deodorising active substance, which can be selected from odour absorbers, deodorising ion exchangers, germ-inhibiting active substances, prebiotically effective components, and inhibitors of the enzymes responsible for the decomposition of sweat, or particularly preferably combinations of these active substances.

Silicates can be used as preferred odour absorbers that also at the same time advantageously enhance the rheological properties of the cosmetic composition. Particularly preferred silicates include, in particular, sheet silicates, and, among these, montmorillonite, kaolinite, illite, beidellite, nontronite, saponite, hectorite, bentonite, smectite and talcum. Further particularly preferred odour absorbers are for example zeolites, zinc ricinoleate, cyclodextrins, certain metal oxides, such as aluminium oxide, as well as chlorophyll.

Odour absorbers can be used in the cosmetic composition preferably in a total amount of from about 0.1 to about 10% by weight, particularly preferably from about 0.5 to about 7% by weight, and in particular preferably from about 1 to about 5% by weight, in each case in relation to the weight of the cosmetic composition.

Preferred cosmetic compositions are exemplified in that they also contain at least one odour absorber, preferably a silicate.

Germ-inhibiting or antimicrobial active substances are understood to be those active substances that reduce the number of skin germs involved in the development of odours or inhibit their growth. These germs include, among others, various species from the group of staphylococci (for example *staphylococcus hominis*), the group of corynebacteria (for example *corynebacterium xerosis, corynebacterium* CDCG2), anaerococci (for example *anaerococcus octavius*) and micrococci.

Organic halogen compounds and halides, quaternary ammonium cations, a number of plant extracts and zinc compounds are also preferred germ-inhibiting or antimicrobial substances. These include, inter alia, triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphen bromide, ammonium phenolsulfonate, benzalkonium halide, benzalkonium cetyl phosphate, benzalkonium saccharinate, benzethonium chloride, cetylpyridinium chloride, lauryl pyridinium chloride, lauryl isoquinolinium bromide, methylbenzethonium chloride. Furthermore, phenol, phenoxyethanol, disodium dihydroxyethyl sulfosuccinylundecylenate, sodium bicarbonate, zinc lactate, sodium phenolsulfonate and zinc phenolsulfonate, ketoglutaric acid, terpenic alcohols such as the particularly preferred farnesol, chlorophyllin-copper complexes, alpha-monoalkyl glycerol ether with a branched or linear saturated or unsaturated, possibly hydroxylated $C_6$-$C_{22}$ alkyl radical, particularly preferably alpha-(2-ethylhexyl)glycerol ether, carboxylic acid esters of mono-, di- and triglycerol (for example glycerol monolaurate, diglycerol monocaprinate), lantibiotics and plant extracts (for example green tea and elements of lime blossom oil) are preferred deodorising active substances.

The one or more of the above-mentioned deodorising active substance(s) can be contained in the cosmetic composition as contemplated herein preferably in a total amount of from about 0.1 to about 10% by weight, more preferably from about 0.2 to about 7.5% by weight, particularly from about 0.3 to about 5% by weight, and in particular preferably from about 0.5 to about 3.0% by weight, in relation to the weight of the cosmetic composition.

Other preferred cosmetic compositions as contemplated herein are exemplified in that they contain at least one encapsulated and/or at least one non-encapsulated fragrance.

Preferably, the encapsulation of fragrances can be selected so that it includes at least one water-soluble encapsulation material. When exposed to moisture, here in particular when exposed to skin moisture or sweat, the water-soluble encapsulation material opens a certain time after application, and the encapsulated fragrance and any other encapsulated active substances, such as skin-cooling active substances, are released with a time delay after application.

Encapsulated and non-encapsulated fragrances, such as perfume oils or mixtures of perfume oils, can be identical or different. Particularly preferred cosmetic compositions are exemplified in that they contain at least one encapsulated and at least one non-encapsulated fragrance, which are different from one another.

Further preferred cosmetic compositions are exemplified in that they contain at least one non-encapsulated fragrance in a total amount of from about 0.1 to about 3% by weight, preferably from about 0.2 to about 1.5% by weight, and particularly preferably from about 0.4 to about 1% by weight, in relation to the total amount of the cosmetic composition in each case.

Further preferred cosmetic compositions are exemplified in that they contain at least one encapsulated fragrance in a total amount of from about 0.01 to about 2% by weight, preferably from about 0.1 to about 1.0% by weight, and particularly preferably from about 0.25 to about 0.5% by weight, in relation to the total amount of the cosmetic composition in each case.

Fragrance compounds are particularly preferred as fragrances or perfume oils, for example the synthetic products of the ester, ether, aldehyde, ketone, alcohol and hydrocarbon type. The preferred phenolic fragrance compounds include, for example, carvacrol. Preferred fragrance compounds of the ester type include, for example, benzyl acetate, methyl anthranilate, ortho-tert-butyl cyclohexyl acetate, p-tert-butyl cyclohexyl acetate, diethyl phthalate, nonanediol-1,3-diacetate, isononyl acetate, isononyl formate, phenylethyl phenylacetate, phenoxyethyl isobutyrate, linalyl acetate, dimethyl benzyl carbinyl acetate, phenylethyl acetate, linalyl benzoate, benzyl formate, ethyl methylphenylglycinate, allyl cyclohexyl propionate, styrallyl propionate, benzyl salicylate, ethyl salicylate, isoamyl salicylate, hexyl salicylate and 4-nonanolide. The preferred ethers include, for example, benzyl ethyl ether; the preferred aldehydes include, for example, linear alkanes with from 8 to 18 C atoms, citral, citronellal, citronellyl oxyacetaldehyde, cyclamen aldehyde, hydroxy citronellal, lilial and bourgeonal; the preferred ketones include, for example, 6-acetyl-1,1,3,4,4,6-hexamethyltetra-hydronaphthalin, para-t-amyl cyclohexanone, 2-n-heptyl cyclopentanone, beta-methyl naphthyl ketone and ionones alpha-isomethyl ionone and methyl cedryl ketone; the preferred alcohols include cinnamyl alcohol, anethole, citronellol, dimyrcetol, eugenol, geraniol, linalool, phenethyl alcohol and terpineol; the preferred hydrocarbons include 1,3,4,6,7,8-hexahydro-4,6,6,7,8,8-hexamethyl-cyclopenta-a-2-benzopyran, hydroxymethyl isopropyl cyclopentane, 3-a-methyl dodecahydro-6,6,9a-trimethylnaphtho-2(2,1-b)furan, isobutyl quinoline as well as terpenes and balms. Mixtures of different fragrances that, together, produce a pleasant scent are particularly preferably used.

Particularly preferred perfume oils can also contain natural mixtures of fragrances, such as those that are available from plant or animal sources, for example pine, citrus, jasmine, ylang ylang, rose or lily oil. Less volatile essential oils that are mostly used as aroma components are also particularly preferred as perfume oils, for example sage oil, chamomile oil, melissa oil, mint oil, cinnamon leaf oil, lime blossom oil, juniper berry oil, vetiver oil, oliban oil, *galbanum* oil, laudanum oil, clove oil, isoeugenol, thyme oil, rose oil, bergamot oil and geranium oil.

Fragrance-free or perfume-free cosmetic compositions can also be preferred as contemplated herein.

Further preferred cosmetic compositions are exemplified in that at least one suspension or thickening agent is contained, preferably selected from hydrophobic clay minerals and fumed silica. Preferred hydrophobic clay minerals are montmorillonite, hectorite and bentonite, in particular disteardimonium hectorite and quaternium-18 hectorite. Commercially available thickening agents provide these hydrophobic clay minerals in the form of a gel. Further preferred thickening agents are fumed silica, for example the commercial products of the Aerosil® series produced by Degussa.

The following examples are intended to explain the present disclosure without limiting it.

EXAMPLES

I. Miscibility

Different oil mixtures were produced by mixing the components listed in Table 1. The miscibility of the oil mixture components was visually assessed at 25° C. and 1013 mbar.

TABLE 1

| Raw material [% by weight] | oil mixture | | | | | |
|---|---|---|---|---|---|---|
| | 1 | 2 | 3 | 4 | 5 | 6 |
| PPG-14 butyl ether | 30.0 | 30.0 | 66.7 | 30.0 | 30.0 | 30.0 |
| Dimethicone 5 cSt | 15.0 | 15.0 | 33.3 | 15.0 | 15.0 | 15.0 |
| 2-ethylhexylpalmitate | 27.5 | 41.25 | — | — | 55.0 | 13.75 |
| Isopropyl myristate | 27.5 | 13.75 | — | 55.0 | — | 41.25 |
| Miscibility | yes | yes | no | yes | yes | yes |

Table 1 shows oil mixtures 1 and 2 as contemplated herein, whereas oil mixtures 3 to 6 are comparison oil mixtures. It can be deduced from Table 1 that, in order to attain a homogeneous mixture at 25° C., at least one ester must be provided in addition to PPG-14 butyl ether and dimethicone 5 cSt (linear polydimethylsiloxane with a kinematic viscosity at 25° C. and a pressure of 1013 mbar of 5 cSt).

II. Feel on Skin

Cosmetic compositions A to F, which consisted of 68% by weight of the respective oil mixture, 2.5% by weight of Bentone 38 V CG (distearyldimonium hectorite, which is a reaction product of distearyldimonium chloride (q.v.) and hectorite) as thickening agent, 1.0% by weight of propylene carbonate as starter for the Bentone 38 V CG, 5% by weight perfume, and 23.5% by weight of aluminium chlorohydrate, were produced from the oil mixtures disclosed in Example I. The feel on skin after application of the respective cosmetic composition was assessed by a team of experts, wherein 1 stood for very dry, 2 for dry, 3 for not dry/not oily/not greasy, 4 for oily/greasy, and 5 for very oily/very greasy. The results are shown in Table 2 below.

TABLE 2

| | Cosmetic composition | | | | | |
|---|---|---|---|---|---|---|
| | A | B | C | D | E | F |
| Score | 3 | 3 | not determinable | 5 | 4 | 4 |

It was found that only the cosmetic compositions A and B as contemplated herein, which contained the specific oil mixture as contemplated herein, had a good fell on skin, which was neither too dry nor too oily or too greasy. The cosmetic composition C could not be assessed, since it demonstrated phase separation. It can be concluded from cosmetic composition D that 2-ethylhexylpalmitate is essential for a good feel on skin of the cosmetic composition. Very small amounts of 2-ethylhexylpalmitate (see cosmetic composition F) indeed led to an improvement of the feel on skin compared to 2-ethylhexylpalmitate-free cosmetic composition D, however an optimal fell on skin (score: 3) could be attained merely by the oil mixture as contemplated herein, including of at least two esters (isopropyl myristate and 2-ethylhexylpalmitate) of at least one linear polydimethylsiloxane which, at 25° C. and a pressure of 1013 mbar, has a kinematic viscosity of from 1 to less than 20 cSt (here: 5 cSt) and PPG-14 butyl ether. The use of 2-ethylhexylpalmitate as sole ester (see cosmetic composition E) also was unable to produce an optimal feel on skin.

III. Antiperspirant Aerosol

Three antiperspirant aerosols as contemplated herein (G, H, I) were produced with the compositions specified in Table 3 by mixing. The formulations G, H and I were each filled into aerosol cans in a ratio by weight of 1:4 with the propellant propane/butane (15/85).

TABLE 3

| Raw material [% by weight] | G | H | I |
|---|---|---|---|
| PPG-14 butylether[1] | 16.0 | 16.0 | 16.0 |
| Isopropylmyristate[2] | 21.0 | 10.5 | 12.0 |
| 2-ethylhexylpalmitate[3] | 21.0 | 31.5 | 30.0 |
| Linear polydimethylsiloxanes, 5 cSt[4] | 10.0 | 10.0 | 10.0 |
| Thickening agent[5] | 2.5 | 2.5 | 2.5 |
| Starter for thickening agent[6] | 1.0 | 1.0 | 1.0 |
| Aluminiumchlorohydrate[7] | 23.5 | 23.5 | 23.5 |
| Perfume | 5.0 | 5.0 | 5.0 |

[1]Ucon Fluid AP, Dow Chemical Company
[2]Isopropyl Myristate, BASF
[3]Cegesoft C24, BASF
[4]Xiameter PMX-200 Fluid 5 CS, Dow Corning Corporation
[5]Bentone 38 V CG, Elementis Specialties
[6]Propylene carbonate
[7]AACH 7172, SummitReheis The antiperspirant aerosols G, H and I were exemplified by a very good antiperspirant effect. The antiperspirant aerosols could be produced very easily by mixing the raw materials, did not demonstrate any tendency to separate and were exemplified by a pleasant feel on skin after application to the skin. The feel on skin was neither too dry nor too oily or greasy, in spite of the absence of volatile cyclic polydimethylsiloxanes.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition comprising an oil mixture in a total amount of from about 40 to about 99% by weight, in relation to the total amount of the cosmetic composition, without taking into consideration any propellant possibly provided, wherein the oil mixture comprises:
   a) at least two esters comprising 2-ethylhexyl palmitate and isopropyl myristate, wherein the ratio by weight of the 2-ethylhexyl palmitate to the isopropyl myristate lies in the range of from about 1 to about 3;
   b) at least one linear polydimethylsiloxane, wherein the linear polydimethylsiloxane, at 25° C. and a pressure of 1013 mbar, has a kinematic viscosity of from about 1 to less than about 20 cSt; and
   c) PPG-14 butyl ether;
   wherein the oil mixture is free of any cyclic polydimethylsiloxanes,
   wherein the total amount of the at least two esters, in relation to the total amount of the oil mixture, is from about 45 to about 70% by weight, and
   wherein the ratio by weight of PPG-14 butyl ether to the total amount of the at least one linear polydimethylsiloxane lies in the range of from about 1.2 to about 2.4.

2. The cosmetic composition according to claim 1, wherein the at least one linear polydimethylsiloxane, at 25° C. and a pressure of 1013 mbar, has a kinematic viscosity of from about 1 cSt to less than about 15 cSt.

3. The cosmetic composition according to claim 1, wherein the total amount of the at least one linear polydimethylsiloxane, in relation to the total amount of the oil mixture, is from about 5 to about 25% by weight.

4. The cosmetic composition according to claim 1, wherein the total amount of PPG-14 butyl ether, in relation to the total amount of the oil mixture, is from about 15 to about 30% by weight.

5. The cosmetic composition according to claim 1, wherein the oil mixture comprises:
   PPG-14 butyl ether in an amount of from about 15 to about 30% by weight, and
   wherein the at least one linear polydimethylsiloxane, at 25° C. and a pressure of 1013 mbar, has a kinematic viscosity of from about 1 to less than about 15 cSt, and the total amount of the at least one linear polydimethylsiloxane is from about 5 to about 25% by weight,
   wherein the amounts relate to the weight of the oil mixture.

6. The cosmetic composition according to claim 1, wherein the oil mixture is contained in an amount of from about 50 to about 85% by weight, in relation to the total amount of the cosmetic composition.

7. The cosmetic composition according to claim 1, wherein the total amount of water, in relation to the total amount of the cosmetic composition, is from 0 to about 5% by weight.

8. The cosmetic composition according to claim 1, wherein the cosmetic composition additionally comprises at least one antiperspirant active substance, in relation to the total amount of the cosmetic composition, of from about 10 to about 40% by weight.

9. The cosmetic composition according to claim 1, wherein it is present in the form of an antiperspirant composition.

10. The cosmetic composition according to claim 1, wherein the total amount of the at least two esters, in relation to the total amount of the oil mixture, is from about 50 to about 65% by weight.

11. The cosmetic composition according to claim 1, wherein the ratio by weight of PPG-14 butyl ether to the total amount of the at least one linear polydimethylsiloxane lies in the range of from about 1.3 to about 2.2.

12. The cosmetic composition according to claim 3, wherein the total amount of the at least one linear polydimethylsiloxane, in relation to the total amount of the oil mixture, is from about 10 to about 17% by weight.

13. The cosmetic composition according to claim 4, wherein the total amount of PPG-14 butyl ether, in relation to the total amount of the oil mixture, is from about 20 to about 25% by weight.

14. A cosmetic composition comprising an oil mixture in a total amount of from about 40 to about 99% by weight, in relation to the total amount of the cosmetic composition, without taking into consideration any propellant possibly provided, wherein the oil mixture comprises:
  a) at least two esters in a total amount of from about 50 to about 65% by weight comprising 2-ethylhexyl palmitate and isopropyl myristate wherein the ratio by weight of the 2-ethylhexyl palmitate to the isopropyl myristate lies in the range of from about 1 to about 3;
  b) at least one linear polydimethylsiloxane in a total amount of from about 10 to about 17% by weight, wherein the linear polydimethylsiloxane or a mixture of two or more linear polydimethylsiloxanes, at 25° C. and a pressure of 1013 mbar, has a kinematic viscosity of from about 1 to less than about 15 cSt; and
  c) PPG-14 butyl ether in an amount of from about 20 to about 25% by weight wherein the ratio by weight of PPG-14 butyl ether to the total amount of all linear polydimethylsiloxanes lies in the range of from about 1.5 to about 2.0;
wherein the cosmetic composition is free of cyclic polydimethylsiloxane, and
wherein the amounts relate to the weight of the oil mixture.

15. The cosmetic composition according to claim 14, wherein the cosmetic composition additionally comprises at least one antiperspirant active substance, in relation to the total amount of the cosmetic composition, of from about 10 to about 40% by weight.

16. The cosmetic composition according to claim 14, wherein it is present in the form of an antiperspirant composition.

17. An antiperspirant cosmetic composition comprising an oil mixture in a total amount of from about 40 to about 99% by weight, in relation to the total amount of the antiperspirant cosmetic composition, without taking into consideration any propellant possibly provided, wherein the oil mixture consists of:
  a) at least two esters in a total amount of from about 50 to about 65% by weight comprising 2-ethylhexyl palmitate and isopropyl myristate wherein the ratio by weight of the 2-ethylhexyl palmitate to the isopropyl myristate lies in the range of from about 1 to about 3;
  b) at least one linear polydimethylsiloxane in a total amount of from about 10 to about 17% by weight, wherein the linear polydimethylsiloxane or a mixture of two or more linear polydimethylsiloxanes, at 25° C. and a pressure of 1013 mbar, has a kinematic viscosity of from about 1 to less than about 15 cSt; and
  c) PPG-14 butyl ether in an amount of from about 20 to about 25% by weight wherein the ratio by weight of PPG-14 butyl ether to the total amount of all linear polydimethylsiloxanes lies in the range of from about 1.5 to about 2.0;
wherein the antiperspirant cosmetic composition is free of cyclic polydimethylsiloxane, and
wherein the amounts relate to the weight of the oil mixture,
the antiperspirant cosmetic composition further comprising at least one antiperspirant active substance, in relation to the total amount of the antiperspirant cosmetic composition, of from about 10 to about 40% by weight.

* * * * *